(12) United States Patent
Van de Pol

(10) Patent No.: US 7,824,716 B1
(45) Date of Patent: Nov. 2, 2010

(54) HERBAL WOMEN'S HEALTH FORMULA

(76) Inventor: Sylvia Van de Pol, 29105 Alessandro Blvd., Moreno Valley, CA (US) 92555

( * ) Notice: Subject to any disclaimer, the term of this patent is extended or adjusted under 35 U.S.C. 154(b) by 0 days.

(21) Appl. No.: 12/082,639

(22) Filed: Apr. 11, 2008

(51) Int. Cl.
 A61K 36/48 (2006.01)
 A61K 36/81 (2006.01)
 A61K 36/45 (2006.01)
 A61K 36/254 (2006.01)
 A61K 36/258 (2006.01)
 A61K 36/889 (2006.01)
 A61K 36/00 (2006.01)

(52) U.S. Cl. .................. 424/727; 424/725; 424/732; 424/760; 424/728; 424/195.17; 424/757; 424/779

(58) Field of Classification Search .................. None
See application file for complete search history.

(56) References Cited

U.S. PATENT DOCUMENTS 6,479,545 B1 * 11/2002 Levinson et al. ............ 514/560

OTHER PUBLICATIONS

Ageless prior art date Oct. 23, 2005 http://web.archive.org/web/20051023125601/http://www.ageless.co.za/herb-motherwort.htm.*
Ginseng prior art date: Feb. 2000 http://www.physicalmag.com/index.php?a=5&p=9.*

* cited by examiner

Primary Examiner—Michele C. Flood
Assistant Examiner—Catheryne Chen
(74) Attorney, Agent, or Firm—Kajane McManus

(57) ABSTRACT

The herbal women's health formula includes a large variety of herbs that are useful in substantially reducing, if not altogether eliminating, a wide range of symptoms specifically related to women.

3 Claims, No Drawings

HERBAL WOMEN'S HEALTH FORMULA

BACKGROUND OF THE INVENTION

1. Field of the Invention

The present invention relates to an herbal women's health formula. More specifically, the formula is designed to promulgate women's health by substantially reducing, if not altogether eliminating, ill effects of symptoms which are of pertinence to women only, 2. Prior Art Although various herbal women's health formulas are known to exist, none have been found to be as effective in such a wide range of problems specifically related to women.

SUMMARY OF THE INVENTION

According to the invention there is provided an herbal women's health formula comprising a number of herbs which coact to substantially decrease, if not altogether eliminate, ill effects of symptoms only of pertinence to women, promulgating women's health.

DESCRIPTION OF THE PREFERRED EMBODIMENT

There is disclosed herein a herbal women's health formula.

In empirical testing the formula has been found to be palliative with respect to a number of various problems which are particular to women.

Such problems include, but are not limited to: bloating, with or without associated pain, uterine and/or back pain, cramping, periodic or mittelschmertz, vaginal/uterine odors, with or without discharge, associated bladder symptoms, with or without control issues, and, if a menstrual cycle has stopped prematurely, it can be started again The formula has to date been created in only small batches, to assure freshness of the herbs used, typically in an amount sufficient to fill approximately 230 "00" sized capsules.

The preferred formulation for one such batch is as follows:

| Tablespoons | Herb |
| --- | --- |
| 1 | Bayberry |
| 2 | Black Cohosh |
| 1 | Blessed Thistle |
| ½ | Cayenne (powder) |
| 1 | Chickweed |
| 1 | Damiana |
| 2 | Dong Quai (powder) |
| 1 | Fenugreek (powder) |
| ½ | Red Ginseng |
| ½ | White Ginseng |
| 1 | Kelp (powder) |
| 2 | Licorice |
| 1 | Marshmallow rt |
| 2 | Pennyroyal |
| 2 | Saw Palmetto |
| 2 | Squaw vine |
| 1 | Sarsaparilla |
| 2 | Mother's wort |
| 1 | Wild Yam |

Each of these herbs has been found efficacious for use by women, as follows:

Cayenne-fruit.
  cleansing of the circulatory and digestive systems.
  prevents muscle aches Chickweed—plant
  reduces water retention during PMS Blessed Thistle-plant
  dissolves blood clots
  urinary tract benefits Black Cohosh-root
  estrogen replacement therapy
  menstrual cramps Damiana-leaves
  balances female hormone levels Dong Quai—
  menstrual cramps Saw Palmetto—fruit
  Menstrual pain
  regulates menstrual cycle Mother's Wort—plant
  premenstrual symptoms
  cramps caused by menstruation Wild Yam
  menstrual symptoms Licorice—root
  premenstrual syndrome
  menopausal symptoms Kelp—herb
  menstruation symptoms Ginseng—root
  muscle relaxation Sarsaparilla—root
  menopausal symptoms
  joint aches and pains Bay Berry—root
  heavy menstrual flow
  vaginal discharge Marshmallow—plant
  aids healing processes Pennyroyal—herb
  menstruation
  cramps Squaw Vine—herb
  17. female problems
  menstruation Fenugreek—medical herb
  healing and reducing inflamation in damaged tissues
  menopausal symptoms
  a strong stimulator of milk production in nursing mothers
  which is perfectly safe provides vitamins A, B, C, high in fiber and protein The combination of herbs as disclosed has also been found to increase the efficacy obtained as compared to use of the herbs individually.

In use an adult female takes two capsules per day at the onset of symptoms, while a teenager takes one capsule per day. Further, if a woman finds that her menses stops too soon, as compared with her normal cycle, she can take one capsule per day until menses begins again, typically within a few days.

As described above, the herbal women's health formula of the present invention has a number of advantages, some of which have been described above, and others of which are inherent in the invention. Also, modifications may be proposed to the formula without departing from the teachings herein. Accordingly the scope of the invention is only to be limited as necessitated by the accompanying claims.

The invention claimed is:

1. An herbal formula for promulgating the health of women comprising 1 tablespoon Bayberry, 2 tablespoon Black Cohosh, 1 tablespoon Blessed Thistle, ½ tablespoon Cayenne powder, 1 tablespoon Chickweed, 1 tablespoon Damiana, 2 tablespoon Dong Quai powder, 1 tablespoon Fenugreek powder, ½ tablespoon Red Ginseng, ½ tablespoon White Ginseng, 1 tablespoon Kelp powder, 2 tablespoon Licorice, 1 tablespoon Marshmallow plant, 2 tablespoon Pennyroyal, 2 tablespoon Saw Palmetto, 2 tablespoon Squaw vine, 1 tablespoon Sarsaparilla, 2 tablespoon Mother's wort, and 1 tablespoon Wild Yam.

2. The formula of claim 1 in the form of a capsule.

3. The formula of claim 1 for treating the symptoms of bloating, uterine or back pain, cramping, mittelschmertz, vaginal or uterine odors, and bladder symptoms.

* * * * *